(12) United States Patent
Rosano et al.

(10) Patent No.: US 9,639,667 B2
(45) Date of Patent: May 2, 2017

(54) PERFORMING DATA ANALYSIS ON CLINICAL DATA

(75) Inventors: Thomas G. Rosano, Albany, NY (US); Merrill S. Ross, New Lebanon, NY (US)

(73) Assignee: ALBANY MEDICAL COLLEGE, Albany, NY (US)

( * ) Notice: Subject to any disclaimer, the term of this patent is extended or adjusted under 35 U.S.C. 154(b) by 1385 days.

(21) Appl. No.: 12/123,897

(22) Filed: May 20, 2008

(65) Prior Publication Data
US 2008/0294350 A1 Nov. 27, 2008

Related U.S. Application Data

(60) Provisional application No. 60/931,069, filed on May 21, 2007.

(51) Int. Cl.
*G06F 19/00* (2011.01)

(52) U.S. Cl.
CPC ........ *G06F 19/3443* (2013.01); *G06F 19/366* (2013.01)

(58) Field of Classification Search
CPC .................................. G06F 19/3443
USPC ........ 702/19, 22, 179, 182; 600/300
See application file for complete search history.

(56) References Cited

U.S. PATENT DOCUMENTS

| | | | |
|---|---|---|---|
| 5,541,854 A | 7/1996 | Yundt | |
| 6,292,761 B1 | 9/2001 | Hancock, Jr. | 702/189 |
| 6,500,117 B1 * | 12/2002 | Hancock, Jr. | G06F 19/345 |
| | | | 128/920 |
| 6,789,019 B2 | 9/2004 | Hirai | 702/19 |
| 6,990,501 B2 | 1/2006 | Beals | 707/104.1 |
| 7,072,794 B2 | 7/2006 | Wittkowski | 702/179 |
| 7,158,890 B2 | 1/2007 | Brumbach et al. | 702/19 |
| 8,388,531 B2 * | 3/2013 | Bush et al. | 600/300 |
| 2002/0095260 A1 | 7/2002 | Huyn | 702/19 |
| 2003/0018633 A1 * | 1/2003 | Horn | 707/4 |
| 2003/0182281 A1 | 9/2003 | Wittkowski | 707/5 |
| 2003/0233197 A1 | 12/2003 | Padilla et al. | 702/20 |
| 2004/0111433 A1 * | 6/2004 | Seto et al. | 707/104.1 |
| 2004/0267568 A1 | 12/2004 | Chandler et al. | 705/2 |
| 2005/0119534 A1 * | 6/2005 | Trost et al. | 600/300 |
| 2007/0106478 A1 | 5/2007 | Jung et al. | 702/19 |

OTHER PUBLICATIONS

Horn et al., "A Robust Approach to Reference Interval Estimation and Evaluation", 1998, Clinical Chemistry, pp. 622-631.*
"Reference Interval Computation using Robust vs. Parametric and Nonparametric Analysis," Horn, Pesce and Copeland, Clinical Chemistry, vol. 45, Issue 12, p. 2284-2285 (1999).

(Continued)

*Primary Examiner* — Ricky Ngon
(74) *Attorney, Agent, or Firm* — Heslin Rothenberg Farley & Mesiti P.C.

(57) ABSTRACT

Reference intervals are established and/or validated based on existing clinical data and exclusion criteria, such as diagnosis coding. A Reference Interval Test Engine is designed to statistically analyze large volumes of existing clinical lab test results to establish and evaluate reference intervals for specific population subgroups and/or to provide other applications.

19 Claims, 9 Drawing Sheets

(56) References Cited

OTHER PUBLICATIONS

"Statistical Methods for Establishing and Validating Reference Intervals," Roger Bertholf, Laboratory Medicine, vol. 37, Issue 5, p. 306-310 (2006).
"The Robust Approach to Reference Interval Estimation and Evaluation," Horn, Pesce and Copeland, Clinical Chemistry, vol. 44, Issue 3, p. 622-631 (1998).
"Reference Intervals for Eighteen Clinical Chemistry Analytes and Fetal Plasma Samples Between Eighteen and Forty Weeks of Pregnancy," Clinical Chemistry, vol. 44, Issue 3, p. 683-685 (1998).
"New Reference Intervals for Thyrotropin and Thyroid Hormones based on National Academy of Clinical Biochemistry Criteria and Regular Untrasonography of the Thyroid," Clinical Chemistry, vol. 51, Issue 8, p. 1480-1486 (2005).
"How to Define and Determine Reference Intervals in the Clinical Laboratory; Approved Guideline—Second Edition," Clinical and Laboratory Standards Institute, C28-A2, vol. 20 No. 13 (Jun. 2000).

* cited by examiner

FIG. 2A

Diagnosis Grouping Update

Enter a search term to shorten the list [Search]

Update Diagnosis groupings below.
31154 records found.

| Diagnosis | ICD9Description | Anemic | Diabetic | Inflammation | Pregnant | Thyroid | Platelet/Abn.. | Custom1 | Custom2 | Custom3 |
|---|---|---|---|---|---|---|---|---|---|---|
| THROMBOCYTOPENIA | | | | | | | | | | |
| THROMBOCYTHEMIA | | | | | | | x | | | |
| THROMBOCYTOPATHY | | | | | | | x | | | |
| THROMBOCYTOPATHY ANEMIA NOS | | x | | | | | x | | | |
| THROMBOCYTOPATHY COAG DEFECT N | | | | | | | x | | | |
| THROMBOCYTOPATHY WBC DISEASE N | | | | | | | x | | | |
| THROMBOCYTOPENIA | | | | | | | x | | | |
| THROMBOCYTOPENIA NOS | | | | | | | x | | | |
| THROMBOCYTOPENIA NOS ANEMIA NO | | x | | | | | x | | | |
| THROMBOCYTOPENIA NOS B12 DEF A | | | | | | | x | | | |
| THROMBOCYTOPENIA NOS BACTEREMI | | | | | | | x | | | |
| THROMBOCYTOPENIA NOS CHRONIC H | | | | | | | x | | | |
| THROMBOCYTOPENIA NOS DM2/NOS U | | | | | | | x | | | |
| THROMBOCYTOPENIA NOS HYPERLIPI | | | | | | | x | | | |
| THROMBOCYTOPENIA NOS IRRITABLE | | | | | | | x | | | |
| THROMBOCYTOPENIA NOS PERIPH VA | | | | | | | x | | | |
| THROMBOCYTOPENIA NOS WBC DISEA | | | | | | | x | | | |
| THROMBOCYTOPENIA NUTROPENIA | | | | | | | x | | | |
| THROMBOCYTOSIS | | | | | | | | | | |
| THROMBOEMBOLISM DX ACUTE | | | | | | | | | | |
| THROMBOLI TO RIGHT HAND | | | | | | | | | | |
| THROMBOPHILIA | | | | | | | | | | |
| THROMBOPHLEBITIS | | | | | | | | | | |
| THROMBOPHLEBITIS ARM NOS | | | | | | | | | | |
| THROMBOPHLEBITIS LEG NOS | | | | | | | | | | |
| THROMBOPHLEBITIS LEG NOS THROM | | | | | | | | | | |
| THROMBOPHLEBITIS NOS | | | | | | | | | | |
| THROMBOPHLEBITIS DMS/NOS U | | | | | | | | | | |

[Submit Changes]

Reference Internal Test Engine - Data Evaluation
Review the selected data and exclude results outside of the desired range.

Test: NA
GENDER: M
Location: ALL
Location Group: na
Multiple Test per patient: excluded
Total Matches: 961

⎫
⎬ —302—
⎭

⎧ Age range: 0 To 10
⎨ Diagnosis: None
⎩ Diagnosis Group: na —304
   Result Range: 122-167
   Result Mean: 138.12 —306
   Standard Deviation: 2.653 —308

Select Method for Outlier Exclusion:
○ 3 Std Dev                    —310
○ NCCLS Guidelines
◉ Manual Selection Below

[Proceed]

|  | Record | Result | Age | Collect Date | Location |  |
|---|---|---|---|---|---|---|
| LOW Cutoff ◉ | 1 | 122 | 6.00 | 04/13/2006 | CLSDC | ○ HIGH Cutoff |
| LOW Cutoff ○ | 2 | 127 | 0.58 | 08/25/2006 | PAS | ○ HIGH Cutoff |
| LOW Cutoff ○ | 3 | 128 | 6.00 | 02/02/2006 | D7N | ○ HIGH Cutoff |
| LOW Cutoff ○ | 4 | 128 | 2.00 | 08/08/2005 | D7N | ○ HIGH Cutoff |
| LOW Cutoff ○ | 5 | 129 | 4.00 | 10/06/2005 | RFE | ○ HIGH Cutoff |
| LOW Cutoff ○ | 6 | 130 | 5.00 | 03/16/2006 | D7N | ○ HIGH Cutoff |
| LOW Cutoff ○ | 7 | 131 | 0.06 | 05/12/2005 | D7N | ○ HIGH Cutoff |
| LOW Cutoff ○ | 8 | 131 | 6.00 | 11/09/2005 | NEPH | ○ HIGH Cutoff |
| LOW Cutoff ○ | 9 | 132 | 7.00 | 03/18/2006 | D7N | ○ HIGH Cutoff |
| LOW Cutoff ○ | 10 | 132 | 2.00 | 05/31/2005 | DNZ | ○ HIGH Cutoff |
| LOW Cutoff ○ | 11 | 132 | 0.25 | 06/07/2005 | EDM | ○ HIGH Cutoff |
| LOW Cutoff ○ | 12 | 132 | 0.25 | 11/22/2005 | D7E | ○ HIGH Cutoff |
| LOW Cutoff ○ | 13 | 132 | 6.00 | 01/11/2006 | D7N | ○ HIGH Cutoff |
| LOW Cutoff ○ | 14 | 132 | 2.00 | 10/15/2006 | D7N | ○ HIGH Cutoff |
| LOW Cutoff ○ | 15 | 133 | 0.01 | 04/02/2006 | D7E | ○ HIGH Cutoff |
| LOW Cutoff ○ | 16 | 133 | 8.00 | 04/27/2006 | LCA | ○ HIGH Cutoff |
| LOW Cutoff ○ | 17 | 133 | 10.00 | 05/11/2005 | EDM | ○ HIGH Cutoff |
| LOW Cutoff ○ | 18 | 133 | 6.00 | 05/09/2005 | EDM | ○ HIGH Cutoff |
| LOW Cutoff ○ | 19 | 133 | 3.00 | 05/12/2005 | EDM | ○ HIGH Cutoff |

FIG. 3

PERFORMING DATA ANALYSIS ON CLINICAL DATA

CROSS-REFERENCE TO RELATED APPLICATION

This application claims priority to U.S. Provisional Application No. 60/931,069, entitled "PERFORMING DATA ANALYSIS ON CLINICAL DATA", filed May 21, 2007, which is hereby incorporated herein by reference in its entirety.

TECHNICAL FIELD

This invention relates, in general, to the evaluation of data, and in particular, to performing analysis on existing clinical laboratory data and for facilitating such analysis.

BACKGROUND OF THE INVENTION

Data analysis is used to gain insight into the information being analyzed and to provide tools used in the evaluation of people, animals, equipment, etc.

One tool used in the evaluation of a person's health is the reference interval. A reference interval is a range of values used in making decisions, such as medical diagnoses, therapeutic management decisions or other physiological assessments. A given reference interval is compared to a result produced from, for instance, a laboratory test performed on a person. If the result falls within the reference interval, then the result is considered within normal range. On the other hand, if the result falls outside of the interval, then the result is considered abnormal.

The clinical laboratory reference interval is the most widely used decision making tool in medicine. The National Committee on Clinical Laboratory Standards (NCCLS) recommends establishing health-associated reference intervals based on age, gender, race and stage of pregnancy, where appropriate. The National Committee on Clinical Laboratory Standards recommends that each reference interval be established by in-house testing (≥120 individuals/interval) or by validated transference of reference intervals from literature or manufacturer. The transference of reference intervals is the predominate practice. The NCCLS guidelines for determination or transference of reference intervals focus on non-clinical reference individuals. One embodiment of the NCCLS guidelines is described in "How to Define and Determine Reference Intervals in the Clinical Laboratory; Approved Guideline—Second Edition," NCCLS, C28-A2, Vol. 20, No. 13, which is hereby incorporated herein by reference in its entirety.

Compliance with the National Committee on Clinical Laboratory Standards is challenging for all hospitals, commercial and practice-based clinical laboratories.

SUMMARY OF THE INVENTION

Thus, a need exists for a capability to facilitate the establishment and/or validation of reference intervals. A further need exists for a capability that facilitates the analysis of existing clinical laboratory data to provide a variety of applications, including, but not limited to, establishing and/or validating reference intervals.

In one aspect of the present invention, reference intervals are established and/or validated by criteria-specific analysis of clinical data aided by a computerized reference interval test engine (RITE) with selection criteria for gender, age, ordering location and/or ordering physician and with exclusion criteria for diagnosis coding, repeat testing and/or defined range of results for associated testing.

As one example, the shortcomings of the prior art are overcome and additional advantages are provided through the provision of a method. The method includes displaying, via a graphical user interface (GUI), to a medical professional underlying test data for a specific population type and providing access thereto, altering, via the GUI, by the medical professional one or more data from the underlying test data based on experience and/or knowledge of the medical professional, the altering including an exclusion input to exclude test data for one or more subjects from the underlying test data, providing, via the GUI, a reference interval range determined after the altering by the medical professional, and making, by the medical professional, a health or medical related decision or assessment using the determined reference interval range and the experience and/or knowledge of the medical professional.

System and computer program products relating to one or more aspects of the present invention are also described and claimed herein.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

FIG. 2A depicts one example of a screen display of a start page of the reference interval test engine used in accordance with one or more aspects of the present invention;

FIG. 2B depicts one example of a screen display used in creating diagnosis groups, in accordance with an aspect of the present invention;

FIG. 3 depicts one example of a screen display of an evaluate page of the reference interval test engine used in accordance with an aspect of the present invention;

DETAILED DESCRIPTION OF THE INVENTION

In accordance with an aspect of the present invention, a capability is provided to facilitate analysis of clinical laboratory data. As an example, analysis of existing clinical laboratory data is performed to determine (i.e., establish and/or validate) reference intervals for specific population subgroups. In one particular example, the analysis is based on input criteria, including exclusion criteria, such as exclusion based on diagnostic coding and/or repeat testing.

In one embodiment, a Reference Interval Test Engine is designed and used to statistically analyze large volumes of existing clinical lab test results and/or data to establish and evaluate reference intervals for specific population subgroups. The Reference Interval Test Engine is, for instance, a software application executed on a processing unit, such as a personal computer, a server, a mainframe computer or any other type of processing unit. However, in other embodiments, one or more components of RITE are developed in hardware, firmware, software or a combination thereof.

Figure 1:
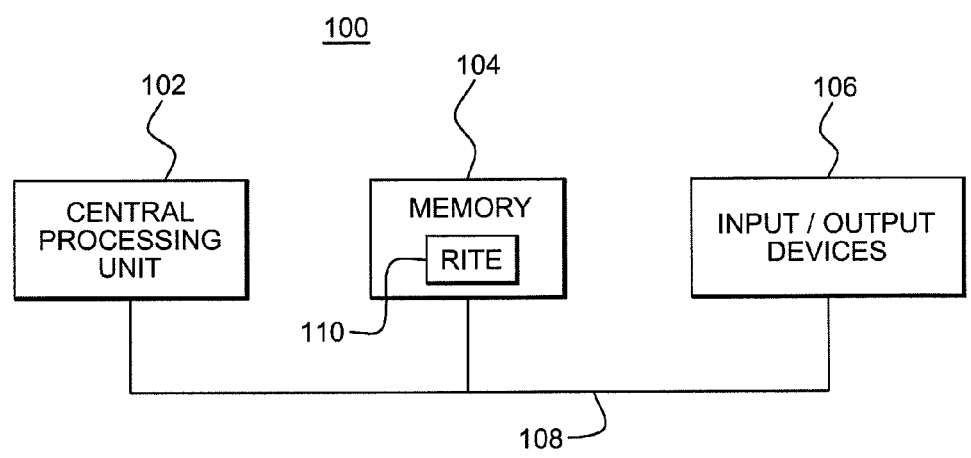
FIG. 1 depicts one embodiment of a processing environment to incorporate and use one or more aspects of the present.

One embodiment of a processing environment to incorporate and use one or more aspects of the present invention is described with reference to FIG. 1. Processing environment 100 includes, for instance, a central processing unit 102, a memory 104 (e.g., main memory), and one or more input/output devices 106 coupled to one another via, for example, one or more buses 108. As one example, at least a portion of the Reference Interval Test Engine 110 is stored in memory 104 and executed by central processing unit 102.

Further details relating to RITE and the establishment and/or validation of reference intervals are described below.

Reference Interval Test Engine (RITE)

RITE is designed to statistically analyze large volumes of existing clinical lab test results and/or data to establish and evaluate reference intervals for specific population subgroups. RITE includes two components, in one example, a database component and an application component, each of which is described below.

Database Design

The data for this application can be exported from practically any lab or Electronic Medical Record system and then imported into the RITE database for analysis. In order to be able to analyze related test results when performing an analysis, an identifier is included for each patient. This identifier is generated during the data file conversion and has no link to any true patient identifiers. This allows for analysis of related test results while maintaining complete de-identification of all patient data.

In one example, the data is exported from a clinical lab system, such as MYSIS. MYSIS is used to record the results of every lab test that is performed on every patient and those results are fed into a larger hospital data repository, where the clinical doctors can review that information to assess a patient and treat a patient.

To populate the database used herein, a text export from the main laboratory computer (which may be the same or different from the computer executing RITE) is performed and that text file is imported to, for instance, the RITE database, which in one example, is a SQL database. Further details of one embodiment of the import are described below.

The data import is from a laboratory data system, which is received from the Lab Information Services department, in one example. That file is imported into an intermediate database, such as an Access database. In the Access database, the data is reviewed, sorted and then an evaluation of the field values are performed. In particular, a determination is made as to whether the data types are correct, and if not, the data is converted. For example, the age field is a text field in this example. In the original database, age is reported as an alphanumeric sequence, if under one year old (e.g., one month). Thus, an Access query is used to take the one month and convert it to a number of days.

In a further example, the result field is also evaluated to remove test results that are not interpretable numerically, such as invalid results or test did not work.

Further, the medical record number (MRN), which is the identifier of the patient, is converted to a sequential number in order to completely de-identify the medical record number from the patient.

Thereafter, the data is exported from the Access database and imported into the RITE database. As examples, the RITE database, access database and the main database(s) may be included on the same processing unit or on one or more processing units coupled to one another. The invention is not limited to a particular configuration. Further, the databases can be other than SQL and/or Access databases, etc. Yet further, in another embodiment, an intermediate database may not be used.

The database used in RITE includes a number of tables, each of which is described below:

1) Results Table (a.k.a., main table)—This table includes the individual records for each test and evaluation criteria and is populated as described above. The fields in each record include, for instance:
   a. Test Name
   b. Result
   c. Age
   d. Gender
   e. Collectdate
   f. Location
   g. De-identified MRN
   h. Diagnosis 2) Diagnosis Table—This table includes each individual distinct diagnosis present in the main data table (a.k.a., Results Table). Group fields are also included in this table. A script allows the system manager to add the individual diagnoses to the groups for consolidated selection on the Start page of the application.

3) Probit Scale Table—This table includes the Probit scaled value and related percentage. The calculated percentage of each result is converted to Probit for the linearization graphs. As is known, the Probit scale is a statistical method used to evaluate probability of a result value in a cumulative distribution of the values represented in either linear or logarithmic format. A Probit number is assigned to every percentage of the total in the file. In this example, the Probit value is reported down to the tenth. Thus, there is a scale number for a percentage of every tenth (0.1, 0.2, 0.3, . . . , 100).

The Probit Scale Table is a published table. In one example, it is copied into Excel and converted into SQL in order to reside in the database used herein. Thus, each time RITE runs the result graphing, it pulls the related Probit number in by using the percent from that result interval and using that to graph and perform statistics on the Probit scale value. Further details regarding the Probit scale table are described in Finney, D. F., *Probit Analysis*, $3^{rd}$ Edition, 1971, Cambridge at The University Press, ISBN 052108041X, which is hereby incorporated herein by reference in its entirety.

4) Location Groups—This table includes each individual collection location and a group field. This allows the locations to be grouped for consolidated selection on the Start page of the application. In one example, this table is also a static table. It is a grouping of locations (e.g., peds for pediatrics, etc.). For instance, inside one hospital, there are about 15 different locations that are exclusively pediatric patients, so the table includes these 15 locations in a pediatrics group. Other groups are also provided, if desired.

Application Design

In one example, RITE is written in Adobe Cold Fusion and uses Microsoft SQL (e.g., Microsoft Data Engine) for the database. Although Cold Fusion is used in this example, this application design can be ported to most any language or platform. In this embodiment, proprietary programming, and associated plug-ins and add-ons are avoided. Similarly, other types of databases may be used.

The application includes, for instance, three main aspects, referred to herein as pages or screens. In this embodiment, each aspect is developed as a web page viewable through, for instance, Internet Explorer®. Internet Explorer® is a registered trademark of Microsoft Corporation. However, in other embodiments, the aspects are other than pages or are pages viewable through other browsers. In one embodiment, the pages include:

1) Start Page—This page defines the selection criteria.
2) Evaluation Page—This page is used to review data matching selection criteria.
3) Results Page—This page is used to view initial results, refine regression, review results, and evaluate for correlation with other test results for exclusion of sub-populations.

Each of the pages is described in further detail below.

Start Page

Figure 2A:
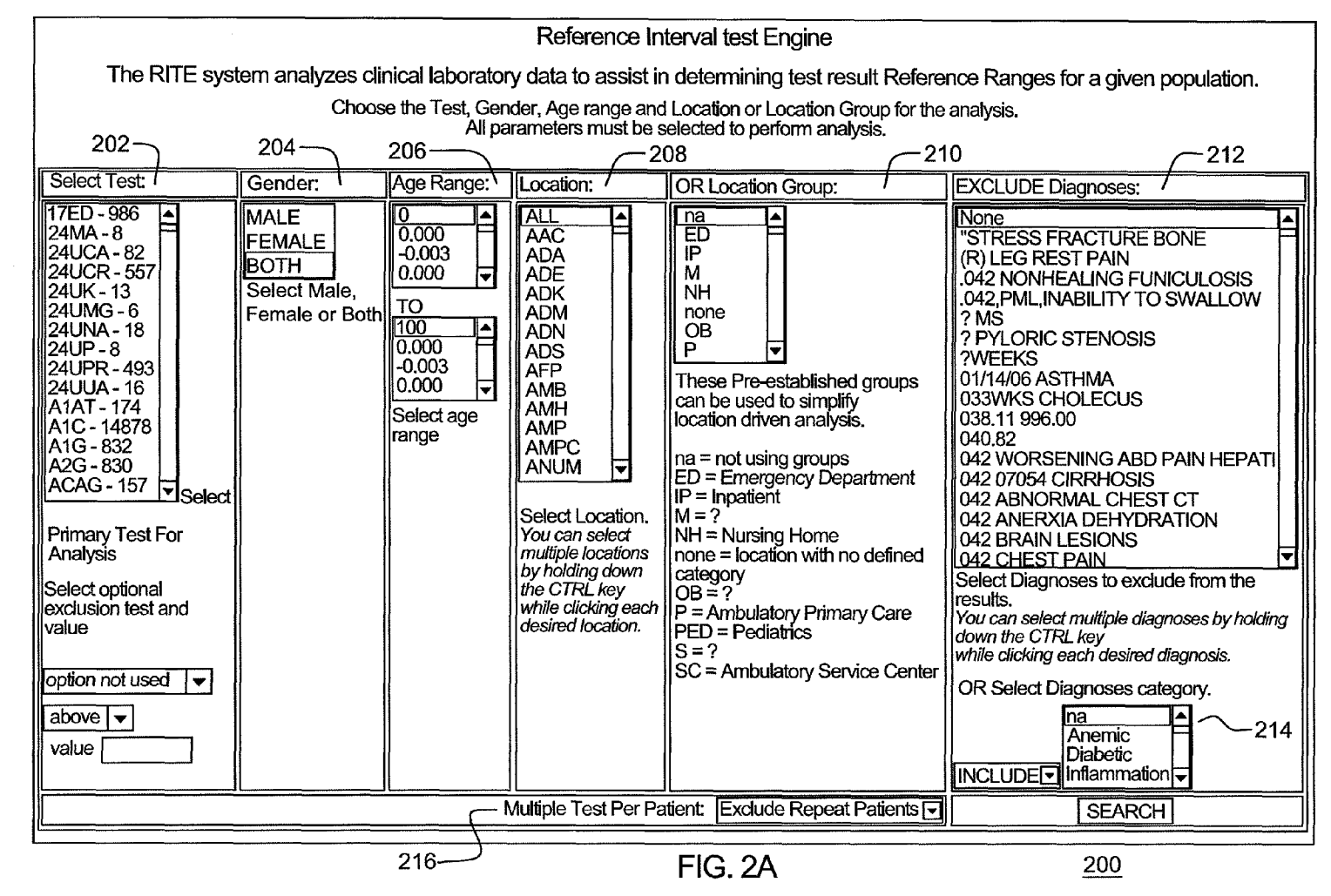

The start page is the first page of the application, and it allows the user to select criteria for the analysis. One example of a screen display of a start page 200 is depicted in FIG. 2A. As shown, there are various criteria that may be selected, including, for instance:

1) Test 202—Select the clinical test to be evaluated. The tests are listed with a total count of the number of actual results for that test. In one example, one test is evaluated at a time. In a further embodiment, the ability to exclude results based on the selection of a different test is also an option. This option allows the user to exclude records if the value of a different selected test is within the exclusion range determined by the user.
2) Gender 204—Select male, female or both for analysis.
3) Select the age range for the analysis 206—Both a start and end age are entered, in this example, to define the range of ages in the analysis.
4) Location 208—Select the location or locations to include in the analysis. This option allows the user to narrow the scope of the analysis, as well as compare different patient populations in separate result sets. As an example, this could be used to analyze the sodium level of inpatients versus outpatients.
    Examples of locations include, for instance, pediatrics, ambulatory (walking) patients, inpatient, outpatient, emergency room, etc.
5) Location group 210—This is another location selection criteria that can be used in place of individual locations. This simplifies the selection of specific patient populations, such as pediatric patients, ambulatory patients, etc.
6) Diagnoses 212—Allows the user to exclude (or include only) results based on the incoming diagnosis. This allows the user to remove records from the results set that could influence the final results of the analysis. This can also be used to compare larger sets of data with more refined sets to analyze the impact of potentially abnormal results on the reference range analysis (e.g., sodium for all patients versus sodium for all patients who are not dehydrated may result in different result ranges).
    Although, in this example, incoming diagnosis(es) are used for exclusion, in further embodiments, intermediate diagnosis(es) and/or final diagnosis(es) may be used, or a combination thereof. An incoming diagnosis is the diagnosis provided by the clinician (e.g., physician, physician assistant, nurse practitioner, etc.) as part of the order for the laboratory test(s) after evaluating the individual. For instance, the clinician evaluates an individual and determines that the individual is dehydrated. This evaluation may include, for instance, physical examination, history, asking one or more questions and/or information provided by a referring clinician. In this example, tests relating to sodium level are ordered and the incoming diagnosis is indicated as dehydration. The individual may be a patient of the organization (e.g., hospital, laboratory, clinic, office, or other health care providers, etc.) performing the analysis or referred to the organization for testing, as examples.
    The final diagnosis is a diagnosis that may or may not agree with the incoming diagnosis.
    One or more diagnoses may be selected for exclusion (or inclusion).
7) Diagnosis Category 214—A separate exclusion/inclusion criteria that combines many incoming diagnoses into a group. Due to the large number of diagnoses (e.g., 30,000 distinct diagnoses for 7,000,000 records), groups are used for exclusion/inclusion conditions (i.e. anemic, pregnant) to simplify analysis input.
    One example of a screen display or form used to create diagnosis groups is depicted in FIG. 2B. To create a group 250 (such as anemic, diabetic, inflammation, pregnant, thyroid, platelet abnormality, a custom group, etc.), the diagnoses 252 are reviewed and if a diagnosis fits in one of the groups, it is placed in the group by placing an indication (e.g., x) in the appropriate column.
8) Multiple Tests per Patient 216 (FIG. 2A)—This can be used to exclude or include records where the same patient had the same test multiple times. If a patient has the same test multiple times, the indication is that there is a reason for multiple tests, usually a value out of the normal range. Therefore, when determining reference ranges, it is preferential, in this example, to use patients who are tested once.

One example of the code used to obtain the information for the Start page is included below:

```
<!--- Query - Get test names and the count of records for each test in the
database for Start page criteria selection --->
<!--- Query - Get list of all Locations for Start page criteria selection --->
<!--- Query - Get list of all Diagnoses for Start page criteria selection --->
<!--- Query - Get list of all Ages for Start page criteria selection --->
<!--- Query - Get list of all Location Groups for Start page criteria
selection --->
<!--- Output HTML Criteria Selection Form Start Page --->
```

Subsequent to selecting the desired criteria, the user submits the form and the application queries the RITE database for the matching records. These records and some basic statistics are then displayed on the evaluation page.

Evaluation Page

The evaluation page allows the user to review records matching the selection criteria. Some basic statistics are available for the user to evaluate and decide outlier removal methodology. One example of a screen display of an evaluation page 300 is depicted in FIG. 3. Examples of the information displayed include:

1) Selection criteria 302 from the Start page are displayed for reference.
2) The result range (lowest test value to highest test value) 304 is displayed.
3) The result mean (average of all selected test values) 306 is displayed.
4) The standard deviation (a measure of the dispersion of the data) 308 is displayed.

The user then decides which outlier removal technique 310 to use. Example techniques include:

1) 3 Std Dev: Determine the standard deviation of the population, multiply it by 3, and include anyone within that value.
2) NCCLS Guidelines: One example of this removal technique is described in "How to Define and Determine Reference Intervals in the Clinical Laboratory; Approved Guideline—Second Edition," NCCLS, C28-A2, Vol. 20, No. 13, which is hereby incorporated herein by reference in its entirety.

Manual Selection: If manual selection is used, then the user reviews all of the matching test records which are displayed in a table on the evaluation page. The result, patient age, collect date and collect location are displayed for review. The user selects the record to use for the low cutoff, and then selects the record to use for the high cutoff. For the low cutoff, any result with a lower value is not displayed. Similarly, for the high cutoff, any result with a higher value than the high cutoff, is not displayed. This page is then submitted and the results page is displayed.

One example of the code used for the Evaluation Page is as follows:

```
<!--- Evaluate whether the TEST exclude/include option was used in
criteria --->
<!--- If TEST exclude/include used, make a query to find all the patients
to
exclude based on the TEST exclude/include criteria --->
<!--- Evaluate whether the Location Group option was used in criteria --->
<!--- If location group used, create a valuelist of the locations in that
group
for use in the main selection query --->
<!--- Evaluate whether the Diagnosis Group option was used in
criteria --->
<!--- If Diagnosis group used, create a valuelist of the Diagnoses in that
group for use in the main selection query --->
<!--- Perform main data query using input criteria --->
<!--- Set a variable for the FIRST result to be used in calculations --->
<!--- Set a variable for the LAST result to be used in calculations --->
<!--- Set a variable for the sum of all results to be used in calculations
--->
<!--- Output HTML Evaluation Page --->
<!--- Set a variable for the Mean --->
<!--- Set Initial value of 0 for sum of all results Variable --->
<!--- Set Initial value of 0 for sum of all results minus mean squared
Variable for use in calculating the variance --->
<!--- Loop over results to add up the results total and calculate the Sum of
Results minus the Mean Squared to calculate variance--->
<!--- Calculate variance --->
<!--- Use variance to calculate Standard Deviation --->
<!--- Output form and pass calculated variables to Results page --->
```

Results Page

Figure 4A:
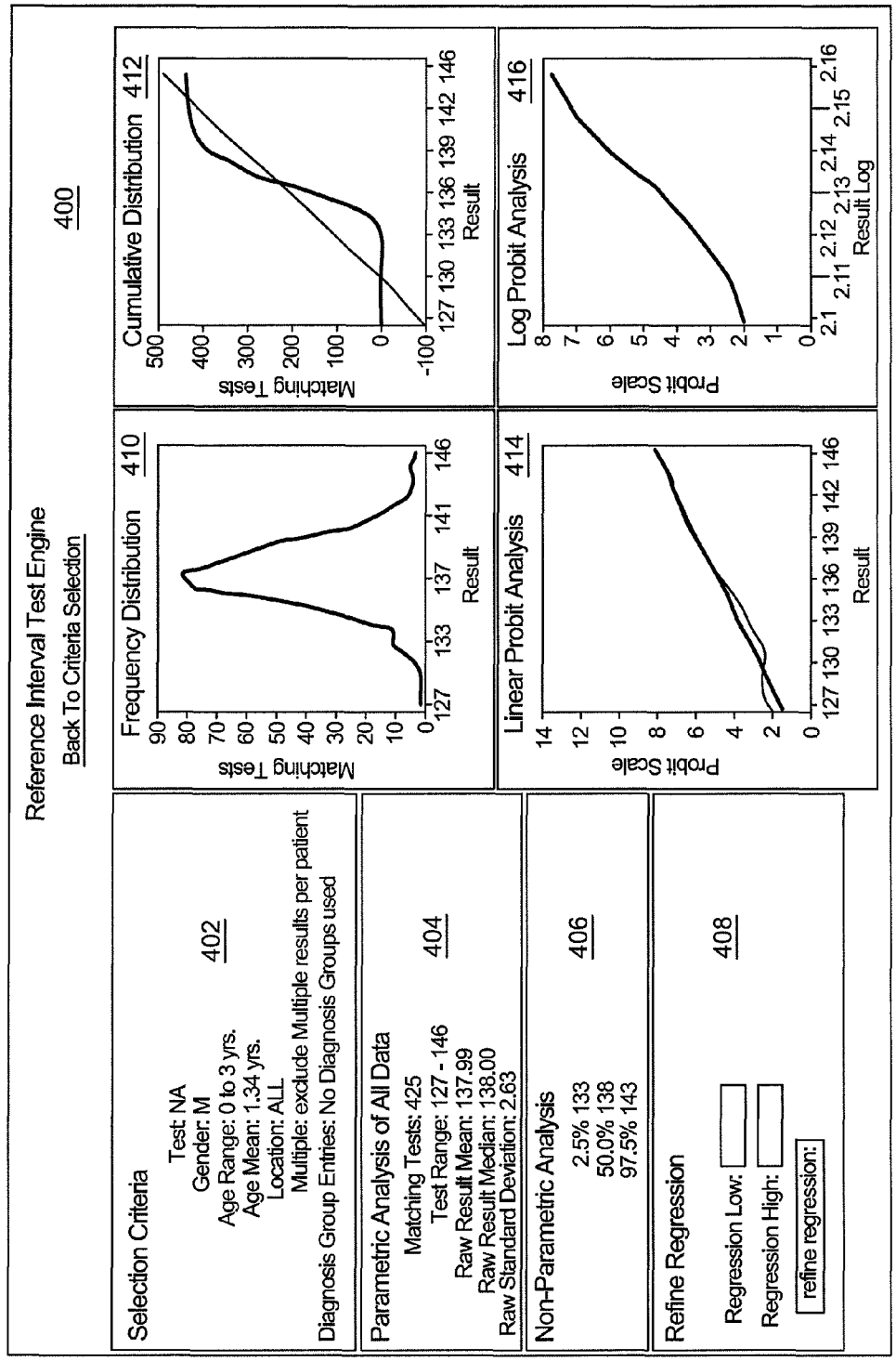
FIG. 4A depicts one example of a results page of the reference interval test engine used in accordance with an aspect of the present invention.

The results page displays the initial results and allows the user to refine the linear regression of the result data. This is where the results range (e.g., reference interval) for the selected population is displayed. One example of a screen display of a results page 400 is depicted in FIG. 4A. As an example, the information displayed includes:

1) Selection criteria 402 are displayed for reference.
2) Parametric Analysis 404—This is statistics on the raw result set. These are used to help determine if the result set is normally distributed which helps to determine which result method to use for the given analysis. The statistics include, for example:
   a. Count of matching tests
   b. Range of results (i.e., reference interval)
   c. Mean
   d. Median
   e. Standard Deviation
3) Non-Parametric analysis 406—95% confidence interval of the non-refined regression. The low (2.5%), mid (50%) and high values (97.5%) are displayed. The resulting non-parametric result range is equal to the 2.5 to 97.5% interval.
4) Refine regression 408—This form allows the user to enter the low and high values for the regressed (best fit) line through the result data. In one example, the user reviews the graph and enters these values manually and submits the form. The regression line along with the final result data is displayed. In a further embodiment, the regression is automatically performed with no user intervention.
5) Graph 1, Frequency Distribution 410—This graph displays the raw results in a non-cumulative fashion. This graphical representation helps the user evaluate the normal (gaussian) versus right or left skewed distribution of the data.
6) Graph 2, Cumulative Distribution 412—This graph displays the results in a cumulative view. This allows for the linear regression to be performed and determines the 2.5-97.5% ile range in which 95% of the results are included. This is referred to as the reference range.

The initial regression is displayed as a straight line (e.g., in one color, such as red). Once the user enters the regression values and submits the form, the results are recomputed and the graph is displayed with an updated regression line (e.g., in a different color, such as green). If the user picked the regression values appropriately, the line will fall on top of the linear portion of the cumulative graph. Although different colored lines are used, in one example, other options are also possible, including different types of lines, different symbols, etc.

7) Graph 3, Linear Probit Analysis 414—This graph displays the cumulative results with the matching test count converted to a probit scale. The user enters the regression values and submits the form, and in response, the final results for the 95% confidence interval are displayed under this graph.
8) Graph 4, Log Probit Analysis 416—This graph can further linearize non-gaussian distributions. Final results for the 95% confidence interval are also displayed under this graph and can be compared to the Linear Probit results.
9) Below the main results window, in one embodiment, may be a separate form (not shown), which can be used to analyze correlating tests. The user can select a separate test and a limit for that test. The user also determines whether the related test values that are either higher or lower than the selected limit are excluded from the analysis. In response to submitting this form, the results are recomputed without the tests that were excluded through the related Test form.

10) At the bottom of the results page (not shown) is a table with each individual result including age, gender, collect location, collect date, and diagnosis for reference.

Figure 4B:
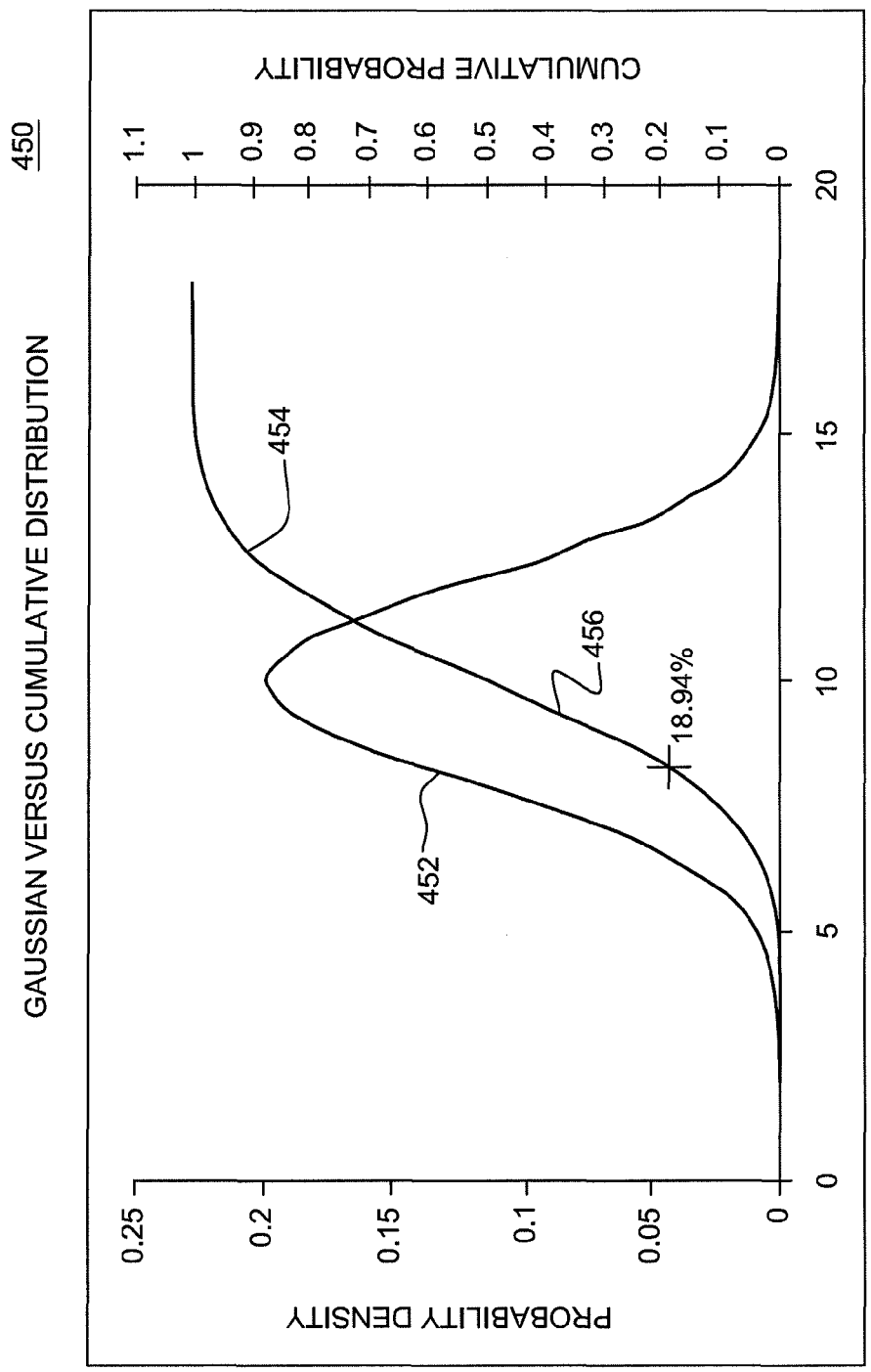
FIG. 4B depicts one example of a graph showing Gaussian vs. cumulative distribution of data, in accordance with an aspect of the present invention.

In one example, the reference range can be depicted graphically in, for instance, a Gaussian vs. cumulative distribution graph 450, an example of which is depicted in FIG. 4B. As shown, the data is displayed in a normally distributed graph 452 a cumulative distribution graph 454. The area where the slope is substantially straight is the reference range 456 for the data.

One example of the code used to provide the Results page is as follows:

```
<!--- Evaluate Outlier Removal method from Eval page.
<!--- Query the main result query to get the data with outliers removed.
This will be the result data query used going forward --->
<!--- Calculate Sum of Results --->
<!--- Set variable for Sum of Results for use in rest of equations --->
<!--- Set variable for Total Rerecord Count --->
<!--- Calculate sum of ages of all records --->
<!--- Create a variable for the first result value --->
<!--- Create a variable for the last result value --->
<!--- Set PARAMETRIC Data initial variables for 2.5, 50 and 97.5 percent
values to the closest integer --->
<!--- Loop over query and get 2.5 percent result by ending loop at variable
set above for 2.5 percent --->
<!--- Loop over query and get 50 percent result by ending loop at variable
set above for 50 percent --->
<!--- Loop over query and get 97.5 percent result by ending loop at
variable set above for 97.5 percent --->
<!--- Evaluate data and determine the increment for the results, i.e. tenths,
hundredths or integers --->
<!--- Calculate the median. Take into account even or odd count of results
and calculate appropriately --->
<!--- Create a New Query to hold the Cumulative values for graphing --->
<!--- Create a record number variable --->
<!--- Create a query to get the values from the Probit scale table in the
database to use for probit graphs and calculations --->
<!--- Create a structure from the query to use for the loop to populate
the new graph data query --->
<!--- Loop over main query to sum the results and populate the graph
output Query --->
<!--- For each increment, query the matching results to count the
number of tests under that increment --->
<!--- For each increment, also count the matching tests individually for the
raw graph --->
<!--- If statement to make sure there was at least one record for the
increment --->
<!--- do nothing since there were no records below or matching this
increment--->
<!--- create the output variables and add them to the graph output
query--->
<!--- Calculate the Percent of the total Y values for this increment --->
<!--- Use the above calculated Y percent to find the corresponding Probit
Number--->
<!--- Add the values to the query--->
<!--- Calculate new mean values (result, probit and age) for the graph
output data --->
<!--- Include subfiles for Linear and probit linear result calculations --->
<!--- Output HTML result page --->
<!--- output regression refine form and pass all current variables
with the form --->
<!--- Output raw data (Frequency Distribution) graph --->
<!--- Output Linear Probit graph and results --->
<!--- Output Raw cumulative distribution graph and results --->
<!--- Output Log Probit analysis --->
<!--- Include subfile for Log Probit result calculations --->
<!--- Output form for user to analyze a related test and the results of that
related test and the impact of those results on the reference range --->
<!--- Output related test data --->
<!--- Output raw result data for review --->
```

Further details relating to statistical analysis are described in Snedecor, George W. and Cochran, William G, *Statistical Methods*, 8$^{th}$ Edition, 1989, Iowa State University Press, ISBN 0813815614, which is hereby incorporated herein by reference in its entirety.

Figure 5:
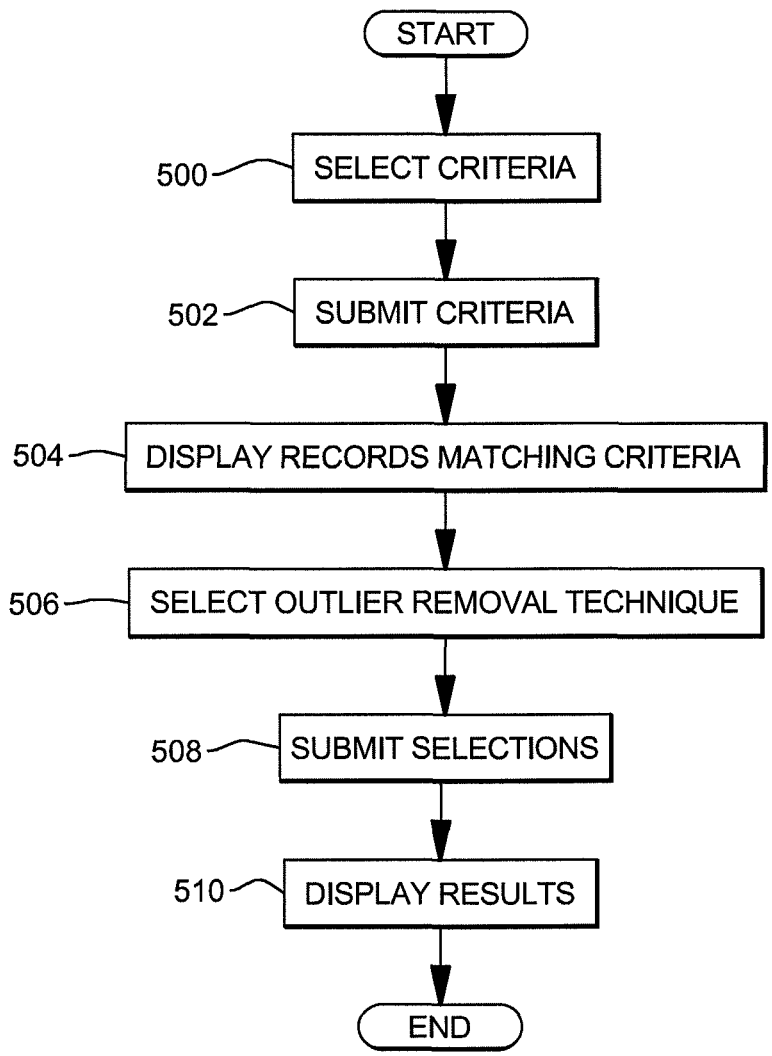
FIG. 5 depicts one embodiment of the logic to determine a reference interval, in accordance with an aspect of the present invention.

Described in detail above is a capability for determining (i.e., establishing and/or validating) reference intervals. A summary of the technique detailed above is described with reference to FIG. 5.

In one embodiment, to establish and/or validate a reference interval, criteria used for the analysis are selected, STEP 500. This criteria is specified and selected using a start page, as an example. Subsequent to selecting the desired criteria, the criteria is submitted (e.g., via a form), STEP 502, and in response thereto, the application queries the database for matching records. The database includes already existing clinical laboratory data of the organization determining the reference interval. That is, the data is not gathered simply to determine a reference interval, but is data that has been obtained for other reasons, such as for health or medical reasons.

The resultant records and optionally, further information, are displayed, STEP 504. It is then possible to select an outlier removal technique to be used in further evaluation of the information, STEP 506. The selection is submitted, STEP 508, and the results are displayed, STEP 510. The results include the reference interval, which is based on the selected criteria. The selected criteria include, in one example, exclusion criteria, such as incoming diagnosis (and/or other diagnosis coding) and/or repeat testing for an individual. With exclusion criteria, records in the data that match the exclusion criteria are eliminated from the analysis and/or results. Thus, with the diagnosis exclusion criteria, as an example, the analysis will increase the prevalence of a population of test results that closely represent the results in a health related population.

In accordance with an aspect of the present invention, a computerized Reference Interval Test Engine (RITE) has been developed and validated for analysis of criteria-based clinical data to assist in the validation of pediatric and adult reference ranges used by clinical laboratories. Scalable capture of de-identified patient data from laboratory information systems has been demonstrated along with flexible selection of inclusion criteria for patient cohorts based on gender, age, ordering location and physician, as examples. Exclusion criteria options include repeat testing, diagnosis coding (such as incoming diagnosis coding and/or final diagnosis coding), and results of associated testing, as examples. Gender and age stratified intervals are determined for each criteria-based cohort by frequency distribution analysis with probit-log transformations.

RITE analysis validated by analysis of a normally distributed set of test data contaminated with increasing population of abnormally low and high test results, showed that contamination with abnormal data up to at least 15% of the total test data did not significantly interfere with the RITE assessment of 95% intervals in the normally distributed data set. Gender and age intervals (95% ile) based on RITE analysis of hematological test results for more than nine thousand criteria-based ambulatory patients was compared with a CDC's reference data from the third National Health and Nutrition Examination Survey conducted by CDC. The table below shows representative data for blood hemoglobin (g/dL) comparison. Comparative 95% intervals in age groups from 1 year to over 70 years demonstrates the applicability of criteria based clinical data analysis in validating either current or transference of reference intervals by the clinical laboratory and the potential for establishing reference intervals when samples from non-clinical reference individuals are not attainable.

|  | Age | | | | | |
| --- | --- | --- | --- | --- | --- | --- |
|  | 1-2 yr | 3-5 yr | 6-9 yr | 9-11 yr | 12-14 yr | 15-19 yr |
| Male RITE | 10.7-13.9 | 11.0-14-2 | 11.4-14.6 | 11.7-15.1 | 11.9-15.8 | 12.9-17.1 |
| Male CDC | 10.5-13.6 | 10.9-13.9 | 11.4-14.5 | 11.7-14.8 | 12.1-16.3 | 13.1-17.1 |
| Female RITE | 10.6-13.8 | 10.9-14 | 11.4-14.8 | 11.5-15.1 | 11.7-15.1 | 11.4-15.1 |
| Female CDC | 10.5-13.7 | 10.9-13.8 | 11.3-14.3 | 11.7-14.7 | 11.3-15.1 | 11.2-14.9 |
|  | Age | | | | | |
|  | 20-29 yr | 30-39 yr | 40-49 yr | 50-59 yr | 60-69 yr | >70 yr |
| Male RITE | 13.8-16.8 | 13.3-16.9 | 13.2-16.8 | 12.9-17 | 12.4-16.9 | 11.1-16.8 |
| Male CDC | 13.7-17.2 | 13.3-17.2 | 13.0-17.1 | 12.6-17.2 | 12.4-17.0 | 11.1-16.9 |
| Female RITE | 11.3-15.4 | 11.3-15.2 | 11.4-15.5 | 11.8-15.3 | 11.5-15.8 | 11.1-15.3 |
| Female CDC | 11.0-15.0 | 10.9-15.3 | 10.5-15.3 | 11.5-15.5 | 11.3-15.5 | 10.9-15.6 |

Figure 6:
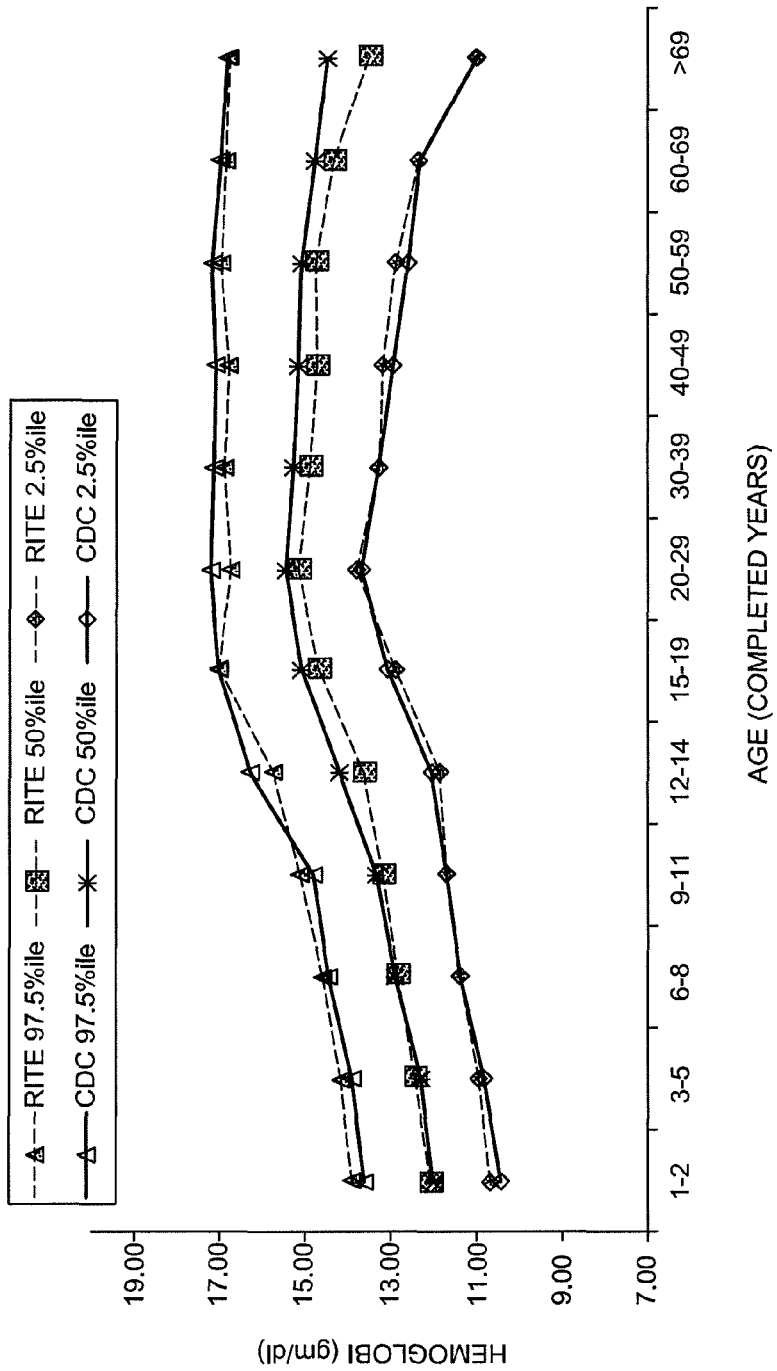
FIG. 6 pictorially depicts the results obtained from one or more aspects of the present invention (RITE) as compared to recommendations of the Center for Disease Control (CDC), in accordance with an aspect of the present invention.

One example of a graph of reference intervals for males is depicted in FIG. 6. This graph shows hemoglobin reference intervals obtained by RITE as compared to CDC recommendations. As depicted, the values obtained by RITE are the same or very close to those recommended by the CDC.

Although in the examples described above, RITE is used to establish and/or validate reference intervals, one or more aspects of RITE may also be applied to other applications, including, but not limited to: determining significant gender and age alterations in diagnostic test values; selectively evaluating subpopulations of patients (e.g., patients with abnormal test results) with other diagnostic tests results through the relational database; and evaluating pathologic test range and advancing diagnostic testing beyond reference interval comparisons to risk assessment for disease states.

Figure 7:
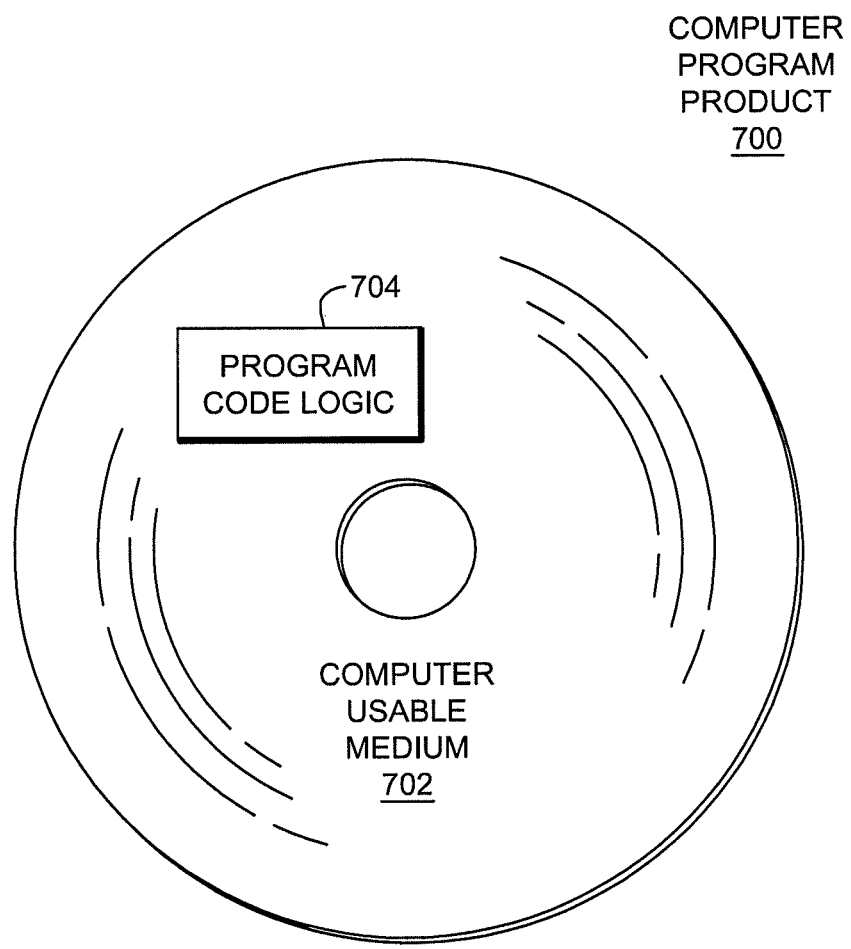
FIG. 7 depicts one embodiment of a computer program product incorporating one or more aspects of the present invention.

One example of an article of manufacture or a computer program product incorporating one or more aspects of the present invention is described with reference to FIG. 7. A computer program product 700 includes, for instance, one or more computer usable media 702 to store computer readable program code means or logic 704 thereon to provide and facilitate one or more aspects of the present invention. The medium can be an electronic, magnetic, optical, electromagnetic, infrared, or semiconductor system (or apparatus or device) or a propagation medium. Examples of a computer readable medium include a semiconductor or solid state memory, magnetic tape, a removable computer diskette, a random access memory (RAM), a read-only memory (ROM), a rigid magnetic disk and an optical disk. Examples of optical disks include compact disk-read only memory (CD-ROM), compact disk-read/write (CD-R/W) and DVD.

A sequence of program instructions or a logical assembly of one or more interrelated modules defined by one or more computer readable program code means or logic direct the performance of one or more aspects of the present invention.

Advantageously, a capability is provided to facilitate the analysis of data. In one example, reference intervals are established and/or validated using exclusion criteria, such as incoming diagnosis information. In particular, in this example, the analysis excludes based on the ICD code, i.e., based on what the clinician (e.g., physician, physician assistant, nurse practitioner, etc.) believes is the condition of the individual being tested for medical or health reasons (not for establishing a reference interval). As other examples, the exclusion criteria includes final diagnosis information, repeat testing and/or combinations thereof and of incoming diagnosis information. As one example, a determined reference interval indicates a normal range for a particular medical condition. As another example, it indicates one or more levels within a disease. Other examples are also possible.

Advantageously, reference intervals that are comparable to those obtained by following NCCLS recommendations are obtained without requiring complex selection procedures required by NCCLS recommendations, such as special testing, filling out of questionnaires, searching for normal, healthy individuals, etc. Instead, the capability described herein uses diagnosis coding and other attributes of already existing clinical data of the organization determining the reference interval, which was obtained for reasons other than determining reference intervals. The individuals used to determine the reference intervals are not normal, healthy individuals in most cases. They are individuals that are being tested for some medical condition. The only normal, healthy individuals that might be included in the data are those that are being tested because of a yearly physical. They are still being tested for a reason other than determining a reference interval.

Advantageously, the capability described herein is retrospective, as opposed to the NCCLS recommendations, which are prospective.

One or more aspects of the present invention enables transference of reference intervals to be validated in each clinical laboratory; and reference intervals to be established when in-house studies or transference is not possible.

Many users of RITE and/or techniques associated thereof can benefit from one or more aspects of the present invention. Potential users of RITE include, but are not limited to hospitals, commercial and practice-based clinical laboratories; laboratory information systems vendors (e.g., Mysis, Cerner, Softpath, etc.); clinical research organizations and grant funded reference interval study programs.

Although various embodiments are described above, these are only examples. For instance, more, less and/or different selection criteria may be used. Further, other programming languages, databases and/or processing environments may be used. Even further, RITE may be used to analyze small quantities of data, as well as large quantities.

A data processing system suitable for storing and/or executing program code is usable that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modems, and Ethernet cards are just a few of the available types of network adapters.

The capabilities of one or more aspects of the present invention can be implemented in software, firmware, hardware, or some combination thereof. At least one program storage device readable by a machine embodying at least one program of instructions executable by the machine to perform the capabilities of the present invention can be provided.

There may be many variations to the steps (or operations) described therein without departing from the spirit of the invention. For instance, the steps may be performed in a differing order, or steps may be added, deleted, or modified. All of these variations are considered a part of the claimed invention.

Although embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A method, comprising:
    displaying, via a graphical user interface (GUI), to a medical professional underlying test data for a specific population type and providing access thereto;
    altering, via the GUI, by the medical professional one or more data from the underlying test data based on experience and/or knowledge of the medical professional, wherein the altering comprises an exclusion input to exclude test data for one or more subjects from the underlying test data;
    providing, via the GUI, a reference interval range determined after the altering by the medical professional; and
    making, by the medical professional, a health or medical related decision or assessment using the determined reference interval range and the experience and/or knowledge of the medical professional.

2. The method of claim 1, wherein the selected diagnosis comprises a group of related diagnoses.

3. The method of claim 1, wherein the one or more inputs comprises a plurality of selected diagnoses.

4. The method of claim 1, wherein the selected diagnosis comprises an incoming diagnosis.

5. The method of claim 1, wherein the selected diagnosis comprises a final diagnosis.

6. The method of claim 1, wherein the exclusion input comprises repeat testing, and wherein the analyzing excludes from analysis data in the existing clinical laboratory data that includes repeat testing for a particular test for an individual.

7. The method of claim 1, wherein the reference interval is determined for an organization, and wherein the existing clinical laboratory data comprises clinical laboratory data previously obtained for individuals associated with the organization.

8. The method of claim 1, wherein the determining the reference interval comprises validating the reference interval.

9. The method of claim 1, wherein the reference interval indicates a reference interval for a particular medical condition.

10. The method of claim 1, wherein the reference interval indicates one or more levels within a disease.

11. The method of claim 1, wherein the medical related decision or assessment comprises whether one or more test results are within a normal range.

12. The method of claim 1, wherein the underlying test data is selected from a database of subjects matching one or more predetermined criteria for determining the reference interval, the selecting based on already existing clinical laboratory data obtained for one or more reasons other than determining the reference interval, wherein the group of subjects has a size at least as large as a conventionally accepted minimum size.

13. The method of claim 1, wherein the underlying test data comprises one or more inputs, the one or more inputs comprising medical test results and other medical information.

14. The method of claim 13, wherein the other medical test information comprises a selected diagnosis.

15. The method of claim 13, wherein the selected diagnosis is an exclusion input.

16. A system of determining reference intervals, said system comprising:
    a memory; and
    a processor in communication with the memory, wherein the system is configured to assist in performing a method, the method comprising:
        displaying, via a graphical user interface (GUI), to a medical professional underlying test data for a specific population type and providing access thereto;
        altering, via the GUI, by the medical professional one or more data from the underlying test data based on experience and/or knowledge of the medical professional, wherein the altering comprises an exclusion input to exclude test data for one or more subjects from the underlying test data;
        providing, via the GUI, a reference interval range determined after the altering by the medical professional; and
        making, by the medical professional, a health or medical related decision or assessment using the determined reference interval range and the experience and/or knowledge of the medical professional.

17. The system of claim 16, wherein the exclusion input comprises repeat testing, and wherein the analyzing excludes from analysis data in the existing clinical laboratory data that includes repeat testing for a particular test for an individual.

18. An article of manufacture comprising:
    at least one non-transitory computer readable medium having stored thereon computer readable instructions, said computer readable instructions when assisting in performing a method of determining reference intervals, the method comprising:
        displaying, via a graphical user interface (GUI), to a medical professional underlying test data for a specific population type and providing access thereto;
        altering, via the GUI, by the medical professional one or more data from the underlying test data based on experience and/or knowledge of the medical professional, wherein the altering comprises an exclusion input to exclude test data for one or more subjects from the underlying test data;

providing, via the GUI, a reference interval range determined after the altering by the medical professional; and making, by the medical professional, a health or medical related decision or assessment using the determined reference interval range and the experience and/or knowledge of the medical professional.

19. The article of manufacture of claim 18, wherein the exclusion input comprises repeat testing, and wherein the analyzing excludes from analysis data in the existing clinical laboratory data that includes repeat testing for a particular test for an individual.

* * * * *